(12) United States Patent
Jeon et al.

(10) Patent No.: US 8,575,335 B2
(45) Date of Patent: Nov. 5, 2013

(54) METHOD OF PREPARING NITROGEN-DOPED GRAPHENE AND NITROGEN-DOPED GRAPHENE PREPARED THEREBY

(75) Inventors: In Yup Jeon, Chungcheongbuk-do (KR); Jong Haom Baek, Ulsan (KR)

(73) Assignee: Unist Academy-Industry Research Corporation, Ulsan (KR)

( * ) Notice: Subject to any disclaimer, the term of this patent is extended or adjusted under 35 U.S.C. 154(b) by 216 days.

(21) Appl. No.: 13/077,777

(22) Filed: Mar. 31, 2011

(65) Prior Publication Data

US 2012/0149897 A1   Jun. 14, 2012

(30) Foreign Application Priority Data

Dec. 10, 2010   (KR) ................. 10-2010-0126262

(51) Int. Cl.
*C07D 471/22*   (2006.01)
(52) U.S. Cl.
USPC ............................................. 540/477
(58) Field of Classification Search
None
See application file for complete search history.

(56) References Cited

U.S. PATENT DOCUMENTS

2011/0245071 A1 * 10/2011 Tanabe .................... 502/180

OTHER PUBLICATIONS

Li et al., J. Am. Chem. Soc., 2009, 131, 15939-15944.*
Nitrogen-Doped Graphene as Efficient Metal-Free Electrocatalyst for Oxygen Reduction in Fuel Cells, Liangi Qu; Jong-Beom Baek; Liming Dai, Acsnano, vol. 4, No. 3, Qu et al., pp. 1321-1326; Published online Feb. 15, 2010 © 2010 American Chemical Society.
Feb. 6, 2009, vol. 323, Science, www.sciencemag.org Nitrogen-Doped Carbon Nanotube Arrays with High Electrocatalytic Activity for Oxygen Reduction, Kuanping Gong; Feng Du; Zhenhai Xia; Michael Durstock; Liming Dai, pp. 760-764.

* cited by examiner

*Primary Examiner* — Sun Jae Loewe
(74) *Attorney, Agent, or Firm* — John B. Hardaway, III; Nexsen Pruet, LLC

(57) ABSTRACT

The present invention relates to a method of preparing a nitrogen-doped graphene comprising preparing a Edge-Functionalized Graphene by binding a graphite with a organic material having amino groups and functional groups such as carboxy acid group through an electrophilic substitution reaction, and heat treating the resultant Edge-Functionalized Graphene, and a nitrogen-doped graphene prepared thereby. According to the present invention, by a more inexpensive and simpler method, a nitrogen-doped graphene can be prepared at higher purity and higher yield. The nitrogen-doped graphene obtained by the present invention has very excellent physical and electric properties, and particularly has a superior oxygen reduction capability, compared with the platinum catalyst used at cathode of a $H_2/O_2$ fuel cell so that it will replace the platinum to lower more the cost of a $H_2/O_2$ fuel cell or to increase its life and further to provide a new turning point for the commercialization of a $H_2/O_2$ fuel cell.

6 Claims, 6 Drawing Sheets

METHOD OF PREPARING NITROGEN-DOPED GRAPHENE AND NITROGEN-DOPED GRAPHENE PREPARED THEREBY

BACKGROUND OF THE INVENTION

1. Field of the Invention

The present invention relates to a method of preparing a nitrogen-doped graphene (hereinafter, referred to as "N-graphene") and a N-graphene prepared thereby. More specifically, the present invention relates to a method of preparing a N-graphene comprising preparing an Edge-Functionalized Graphene (hereinafter, referred to as "EFG") by binding an organic material having amino groups and functional groups such as carboxyl group with graphite through an electrophilic substitution reaction, specifically, the Friedel-Crafts acylation reaction and heating the resultant EFG, and a N-graphene prepared thereby.

2. Background of the Related Art

A graphene is classified as one of new materials which are the most remarkable in the future, as a material with very excellent physical and electronic properties There are various reported methods of preparing a graphene with such excellent physical properties. Examples of the methods may include a mechanical exfoliation method, a chemical exfoliation method, a exfoliation-reinsertion-expansion method, a chemical vapor deposition method, an epitaxy synthesis method and the like.

The mechanical exfoliation method has a problem that the final yield is extremely low, and the chemical exfoliation method has a problem that there remains many defects in graphene so that graphene-inherent excellent physical and electric properties are decreased. The exfoliation-reinsertion-expansion method has a problem that substantial yield of graphene is very low and interlayer contact resistance is high due to used surfactants so that the method does not exhibit satisfactory electric properties. The chemical vapor deposition method has problems such as a complicated process, the requirement of a heavy metal catalyst, and many limitations in mass production. The epitaxy synthesis method has disadvantages such as a poor electric property of the produced graphene and very expensiveness of the substrate.

Meanwhile, although the platinum catalyst is considered as the most efficiency one for a $H_2/O_2$ fuel cell, it has disadvantages such as high cost, decreased performance caused by CO poisoning, and limited amount.

Although the research for high performance catalyst capable of replacing the Pt catalyst and Ru catalyst has been conducted for more than 10 years until now, it is difficult to realize the catalyst.

Therefore, the catalyst research for a $H_2/O_2$ fuel cell has fundamentally focused on the efficiency use of platinum. Largely, the research for increasing the reaction surface by controlling the size of particle of platinum to nano size and the research for enhancing reactivity using carriers of various structures and alloy have been conducted.

As the particle size of platinum is smaller, the particle surface thereof per weight increases and the distribution is also higher, which is advantageous in the manufacture of lowly carried platinum catalyst. Therefore, the research for reducing the used amount of catalyst by controlling the particle size of catalyst or using carrier has been conducted, and many results have been reported.

Because of such reasons, many researchers have studied a carrier having various structures such as carbon particle, carbon nano tube, porous carbon particle and the like for various objects. As a result of such study, the used platinum amount has been reduced to a hundredth during several decades. Now, although it is reported that the carried amount of Pt in the a range of 0.2~0.4 $mg/cm^2$ has a best efficiency, it is generally accepted that the amount of platinum should be reduced to a fifth or less from the current technology for commercialization. Ultimately, the amount should be reduced to a tenth or less from the current technology.

Although largely the reduction of the carried amount of platinum and the efficient dispersion of platinum, and the development of non-platinum catalyst are pursued all over the world, including the U.S.A., Japan and Europe, both reduction of cost and enhancement of performance do not yet meet practical use.

The research team of professor Dai in the U.S.A. has developed an electrode which has a longer life and about four times more excellent performance than platinum (Pt) catalyst using a vertically cultured carbon nano tube doped with nitrogen by metal-free oxygen reduction catalyst for a $H_2/O_2$ fuel cell (2009, Science).

Further, there was already a report that by estimating the performance of N-graphene as a $H_2/O_2$ fuel cell catalyst, N-graphene shows a similar catalyst activity to nitrogen-doped carbon nano tube (2010, ACS Nano).

These methods may be a very good research result showing that a nitrogen-doped carbon material can replace a platinum catalyst.

However, since the used method for preparing the carbon nano material is a chemical vapor deposition (CVD) method, it has a many difficulties to be practically applied industrially.

SUMMARY OF THE INVENTION

It is an object of the present invention to provide a method of preparing a metal-free oxygen reduction catalyst for a $H_2/O_2$ fuel cell, which is capable of solving the problems in the conventional methods as discussed above. That is, N-graphene is prepared as a oxygen reduction catalyst not containing metal such as platinum, the N-graphene is prepared by a method other than the CVD method, and such preparation method should be conveniently applicable in industry.

In addition, it is an object of the present invention to provide nitrogen-doped graphene prepared by the method according to the present invention described as above.

To accomplish the objects, according to one aspect of the present invention, there is provided a method of preparing N-graphene comprising 1) reacting an organic material having one or more amino groups and one or more functional groups selected from the group consisting of carboxylic acid group, amide group, sulfonic acid group, carbonylchloride group and carbonylbromide group with graphite in a reaction medium containing polyphosphoric acid and phosphorus pentoxide, thereby the graphite being exfoliated with the functional group of the organic material grafted to the graphite to prepare organic material-grafted graphene; and 2) heat treating the prepared organic material-grafted graphene at a temperature of 300 to 1,200° C.

The organic material is alkane having 1 to 13, preferably 5 to 13 carbon atoms, alkene having 2 to 13, preferably 5 to 13 carbon atoms, alkyne having 2 to 13, preferably 5 to 13 carbon atoms, cycloalkane having 3 to 13, preferably 5 to 13 carbon atoms, arene having 7 to 19, preferably 11 to 19 carbon atoms or arylalkane having 7 to 19, preferably 11 to 19 carbon atoms, which have amino groups and the above functional groups. The alkane, alkene, alkyne, cycloalkane, arene and arylalkane are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, phenoxy and the combination thereof.

Preferably, the organic material may be aminobenzoic acid, diaminobenzoic acid, aminobenzoamide or diaminobenzoamide, which are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, phenoxy and the combination thereof.

More preferably, the organic material may be a compound selected from the group consisting of 3-aminobenzoic acid, 4-aminobenzoic acid, 3-(4-aminophenyl)benzoic acid, 3-(3-aminophenyl)benzoic acid, 4-(4-aminophenyl)benzoic acid, 4-(3-aminophenyl)benzoic acid, 5-aminoisophthalic acid, 3-(4-aminophenoxy)benzoic acid, 3-(3-aminophenoxy)benzoic acid, 4-(4-aminophenoxy)benzoic acid, 4-(3-aminophenoxy)benzoic acid, 3,4-diaminobenzoic acid, 3,5-diaminobenzoic acid, 3-aminobenzoamide and 4-aminobenzoamide.

In addition, the heat-treatment is conducted for 10 minutes to 12 hours.

In addition, the heat-treatment is conducted under the atmosphere of gas selected from the group consisting of methane, hydrogen, nitrogen, helium, neon, argon and the combination thereof.

Further, the object of the present invention is achieved by N-graphene prepared by the above preparation method according to the present invention.

The N-graphene contains 0.01 to 5 wt % of nitrogen.

In the present invention, when the organic material having amino groups and functional groups such as a carboxylic acid group is reacted with graphite in a reaction medium containing polyphosphoric acid/phosphorus pentoxide, the organic material acts as a wedge, being grafted to graphite through electrophilic substitution reaction with graphite, resulting in the exfoliation of graphite to prepare edge-functionalized graphene.

Such method of preparing graphene enables graphene to be prepared having a much higher purity, compared with a general chemical exfoliation method, enables graphene to be obtained at a high yield, compared with the mechanical exfoliation method using scotch tape, and enables graphene to be prepared in using an inexpensive and simple process, compared with the CVD method.

According to the present invention, an unnecessary portion of the organic materials are removed by heat treating organic material having amino groups-grafted graphene and N-graphene can be produced massively by introducing nitrogen to the graphene structure.

While the platinum catalyst acts as an obstacle to broad commercialization of $H_2/O_2$ fuel cell due to insufficient catalyst activity and stability, and high cost thereof, the N-graphene according to the present invention has very excellent physical and electric properties, and particularly has superior oxygen reduction capability, compared with the above platinum catalyst and thus may replace the platinum catalyst used as oxygen reduction catalyst in the cathode of a $H_2/O_2$ fuel cell.

Therefore, N-graphene having a high oxygen reduction characteristic and a stability which will replace the platinum in order to lower more of the cost of a $H_2/O_2$ fuel cell or increase its life will provide a new turning point for the commercialization of a $H_2/O_2$ fuel cell.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
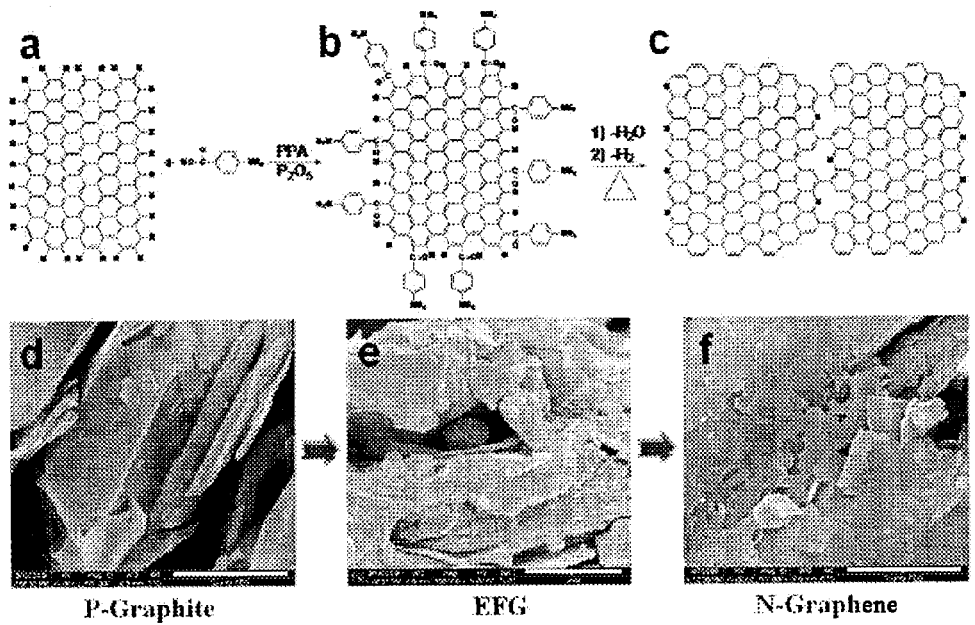
FIG. 1 is a reaction formula schematically representing the preparation reaction of N-graphene according to the present invention, and a field emission scanning electron microscope image of each reactant and product.

The N-graphene according to the present invention can be obtained by reacting an organic material having amino groups and functional groups such as carboxylic acid group with graphite to prepare organic material-grafted graphene, and heat treating the organic material-grafted graphene.

Accordingly, a method of preparing organic material-grafted graphene is first described, a method of preparing N-graphene by heat treating the organic material-grafted graphene is described, and then N-graphene prepared by the preparing method is described.

The method of preparing organic material-grafted graphene according to the present invention comprises reacting an organic material having one or more amino groups and one or more functional groups selected from the group consisting of carboxylic acid group, amide group, sulfonic acid group, carbonylchloride group and carbonylbromide group with graphite in a reaction medium containing polyphosphoric acid and phosphorus pentoxide. The functional groups of the organic material are grafted to the graphite and at the same time, the graphite is exfoliated to prepare organic material-grafted graphene.

The polyphosphoric acid is a weak acid having a pH of 1 to 4, preferably 2 to 3. Such polyphosphoric acid has an advantage that it does not particularly affect the inherent structure of graphite while acting as a weak acid so that it does not attenuate inherent characteristics of graphite. Further, the polyphosphoric acid is a polymeric acid having viscosity and thus provides a strong shear force upon mechanically stirring. Further, such polyphosphoric acid has an advantage to be conveniently removed since it is well dissolved in water.

The phosphorus pentoxide is a dehydrating agent and removes water produced by reaction between organic material and graphite. Since phosphorus pentoxide reacts on water to be changed into a polyphosphoric acid, it does not have other effect on the reaction except for the acceleration of the reaction between graphite and organic material and also has an advantage that it is conveniently removed because it is well dissolved in water.

The polyphoric acid is contained in an amount of 65 wt % to 85 wt %, preferably 74 wt % to 83 wt %, based on the total weight of reaction medium in the reaction medium, and the phosphorus pentoxide is contained in an amount of 15 wt % to 35 wt %, preferably 17 wt % to 26 wt %, in the reaction medium.

In the reaction medium containing of polyphosphoric acid and phosphorus pentoxide according to the present invention, oxidation of graphite does not occur, and only selective functionalization in the edge of graphite, that is, a reaction that organic material is grafted to the edge of graphite occurs.

The functional group of organic material is selected from the group consisting of carboxylic acid group, amide group, sulfonic acid group, carbonylchloride and carbonylbromide group.

Preferably, the functional group of organic material is selected from the group consisting of —COOH, —CONH$_2$, —CONR'H, —CONR'R", —SO$_3$H, —COCl and —COBr, wherein R' and R" are each independently an alkyl group having 1 to 5 carbon atoms, an aryl group having 6 to 10 carbon atoms, or an aralkyl group having 6 to 10 carbon atoms, wherein the alkyl group, the aryl group, and the aralkyl group are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, phenoxy and the combination thereof.

The organic material is alkane having 1 to 13, preferably 5 to 13 carbon atoms, alkene having 2 to 13, preferably 5 to 13 carbon atoms, alkyne having 2 to 13, preferably 5 to 13 carbon atoms, cycloalkane having 3 to 13, preferably 5 to 13 carbon atoms, arene having 7 to 19, preferably 11 to 19 carbon atoms or arylalkane having 7 to 19, preferably 11 to 19 carbon atoms, which have amino groups and the above functional groups. The alkane, alkene, alkyne, cycloalkane, arene and arylalkane are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, phenoxy and the combination thereof.

More preferably, the organic material may be aminobenzoic acid, diaminobenzoic acid, aminobenzoamide, or diaminobenzoamide, which are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, phenoxy and the combination thereof.

Most preferably, the organic material may be a compound selected from the group consisting of 3-aminobenzoic acid, 4-aminobenzoic acid, 3-(4-aminophenyl)benzoic acid, 3-(3-aminophenyl)benzoic acid, 4-(4-aminophenyl)benzoic acid, 4-(3-aminophenyl)benzoic acid, 5-aminoisophthalic acid, 3-(4-aminophenoxy)benzoic acid, 3-(3-aminophenoxy)benzoic acid, 4-(4-aminophenoxy)benzoic acid, 4-(3-aminophenoxy)benzoic acid, 3,4-diaminobenzoic acid, 3,5-diaminobenzoic acid, 3-aminobenzoamide and 4-aminobenzoamide.

The organic material is reacted with graphite in a weight ratio of 4:1 to 1:8, preferably 1:1 to 1:4, in a reaction medium containing polyphosphoric acid and phosphorus pentoxide.

At this time, the reaction temperature is in the range of 100 to 160° C., preferably 120 to 140° C. When the reaction temperature is less than 100° C., there is a problem that the reaction does not occur. When the reaction temperature is higher than 160° C., there is a problem that side reactions much occur.

The reaction time is in a range of 12 to 120 hours, preferably, 60 to 84 hours. When the reaction time is less than 12 hours, the reaction is not completed and when the reaction time is higher than 120 hours, the further reaction does not proceed.

The reaction is carried out after 0.01 to 40 parts by weight of graphite is put into 100 parts by weight of the reaction medium.

The organic material acts as a wedge, being grafted to graphite through an electrophilic substitution reaction of the organic material with graphite, specifically Friedel-Crafts acylation, resulting in the exfoliation of graphite, to prepare egde-functionalized graphene, i.e. organic material-grafted graphene.

That is, graphite is reacted with organic material in a medium containing polyphosphoric acid and phosphorus pentoxide so that edge-located bonds between graphenes which are each layer constituting graphite are substituted with covalent bonds between the functinalized groups of organic material and graphene-edge carbons. The organic material also acts as a wedge resulting in the exfoliation of the graphite to prepare organic material-grafted graphene.

Amino groups in the organic material act as a nitrogen source upon later heat treating organic material-grafted graphene to prepare N-graphene according to the present invention.

As such, when organic material is reacted with graphite in a reaction medium containing polyphosphoric acid and phosphorus pentoxide, organic material-grafted graphene is produced as described above, however, in the reaction product, in addition, unreacted graphite and organic material as well as polyphosphoric acid and phosphorus pentoxide coexist.

In order to remove polyphosphoric acid and phosphorus pentoxide and unreacted organic material from the reaction product in which various compounds exist as such, the reaction product is washed using water and then washed using alcohol such as methanol. Thereafter, the resultant washed material may be dried using a method such as drying under reduced pressure and lyophilizing.

Upon lyophilizing, since the lyophilizing is carried out maintaining space between the produced organic material-grafted graphenes as it is, when the lyophilized material obtained through such lyophilizing is again dissolved in a solvent, the solvent can penetrate the space better between organic material-grafted graphenes. As a result, organic material-grafted graphenes are better dissolved, allowing for the process to more conveniently proceed thereafter.

Since the unreacted graphite and organic material-grafted graphene are mixed in the washed material before drying the washed material by a method such as drying under reduced pressure and lyophilizing, such washed material may be dissolved in a solvent and centrifuged so that only organic material-grafted graphene may be isolated. However, in preparing N-graphene according to the present invention, the washed material in which unreacted graphite and organic material-grafted graphene are mixed may be used as it is.

The solvent is dependent on the kind of bound organic material in the organic material-grafted graphene. The solvent may be selected from, but is not limited to, the group consisting of water, methanol, ethanol, isopropyl alcohol, toluene, benzene, hexane, heptane, m-cresol, ethyl acetate, carbon disulfide, dimethyl sulfoxide, dichloromethane, dichlorobenzene, chloroform, carbon tetrachloride, aceton, tetrahydrofuran, dimethylacetamide, N-methylpyrrolidone, dimethylformamide, acetic acid and the combination thereof.

The centrifugation is carried out at a speed of 1,000 to 15,000 rpm, preferably 7,000 to 12,000 rpm for 30 seconds to 20 minutes, preferably 2 minutes to 15 minutes, to isolate organic material-grafted graphene. When the centrifugation speed is less than 1,000 rpm or the centrifugation time is less than 30 seconds, the isolation is not well achieved. When the centrifugation speed is higher than 15,000 rpm or the centrifugation time is more than 20 minutes, there is a danger that the centrifugal tube may be broken.

The method of preparing N-graphene according to the present invention comprises heat treating the organic material-grafted graphene prepared by a method of preparing organic material-grafted graphene of the present invention using a general electric furnace at a temperature of 300 to 1,200° C., preferably 500 to 1,100° C., more preferably 800 to 1,000° C., for a time period of 10 minutes to 12 hours, preferably 30 minutes to 6 hours, more preferably 1 to 4 hours.

For the heat-treatment, a portion of organic material covalently bonded to the edge of graphene acts as in-situ N-doping and C-welding feedstock to prepare nitrogen-introduced graphene.

When heat treating at a temperature of less than 300° C., there is a problem that nitrogen doping on graphene is not well achieved, and when heat treating at a temperature of higher than 1,200° C., there is a problem that graphene is lost.

In addition, when the heat-treatment is conducted for a time period of less than 10 minutes, there is a problem that nitrogen doping on the graphene is not well achieved, and when the heat-treatment is conducted for a time period of more than 12 hours, further doping is not achieved.

In addition, the heat-treatment is conducted under the atmosphere of gas selected from the group consisting of methane, hydrogen, nitrogen, helium, neon, argon and the combination thereof. When the heat-treatment is conducted in the presence of gas such as oxygen, there are problems that not only nitrogen doping is not achieved, but also graphene is burned. Therefore, it is preferable that the heat-treatment is conducted in the presence of inert gas.

The N-graphene according to present invention is prepared by a method of preparing the N-graphene and comprises 0.01 to 5 wt % of nitrogen.

Hereinafter, the present invention will be described in more detail by examples. These examples are provided for clear understanding of the present invention and are not intended to restrict the scope of the present invention. The present invention will be determined by the appended claims.

Example 1-1

Preparation of Organic Material-Grafted Graphene 0.5 g of graphite and 0.5 g of 4-amino benzoic acid were put into 25 g of reaction medium containing 20 g of polyphosphoric acid (PPA), polyphosphoric acid (115% $H_3PO_4$ basis) purchased from Sigma Aldrich and 5 g of phosphorus pentoxide ($P_2O_5$) and stirred under dry nitrogen purge at 130° C. for 72 hours to react the graphite with 4-aminobenzoic acid.

The initially black mixture became lighter and viscous. At the end of the reaction, the color of the mixture turned tanned brown. After the termination of reaction, the resultant product was treated with water for three days, and then with methanol for three days using Soxhlet to remove polyphosphoric acid, phosphorus pentoxide and unreacted reactants such as unreacted 4-aminobenzoic acid. Thereafter, the resultant remainder was lyophilized under reduced pressure to obtain 0.74 g (79% yield) of tanned brown powder.

FIGS. 1a and 1b show a reaction of preparing organic material-grafted graphene wherein graphite (P-graphite) is reacted with 4-aminobenzoic acid in reaction medium containing polyphosphoric acid/phosphorus pentoxide to prepare organic material-grafted graphene (EFG).

FIG. 1d is a magnified image of P-graphite used in such reaction using the field emission scanning electron microscope (FE-SEM, LEO 1530FE and FEI NanoSem 200). FIG. 1e is a magnified image of organic material-grafted graphene (EFG) prepared by such reaction using the field emission scanning electron microscope (scale bar is 1 μm).

Example 1-2

Preparation of N-Graphene

The organic material-grafted graphene (EFG) obtained in the Example 1-1 was heat treated using an electric furnace under nitrogen atmosphere at 900° C. for 2 hours to obtain N-graphene FIGS. 1b and 1c show a preparation reaction of such N-graphene wherein by heat treating organic material-grafted graphene (EFG), unnecessary organic material portions are removed and nitrogen is introduced into the structure of grapheme.

FIG. 1f is a magnified image of N-graphene prepared by such reaction using the field emission scanning electron microscopy (scale bar is 1 μm).

Experimental Example 1

Elemental Analysis and XPS

For graphite used in the example 1-1, the organic material-grafted graphene obtained in the example 1-1 and N-graphene obtained in the example 1-2, elemental analysis was conducted with Thermo Scientific Flash 2000 and X-ray photoelectron spectroscopy (XPS) was conducted on Thermo Fisher K-alpha. The results are shown in the following Table 1 and FIG. 2.

TABLE 1

| Sample | | Elemental Analysis | | | | XPS | | |
|---|---|---|---|---|---|---|---|---|
| | | C (%) | H (%) | N (%) | O (%) | C (%) | N (%) | O (%) |
| P-graphite | Calcd | 100.0 | 0.00 | 0.00 | 0.00 | 100.0 | 0.00 | 0.00 |
| | Found | 97.64 | BDL* | BDL* | 0.005 | 85.05 | BDL* | 14.92 |
| EFG | Calcd | 89.90 | 1.70 | 3.93 | 4.48 | 89.90 | 4.48 | 3.93 |
| | Found | 86.41 | 1.55 | 3.81 | 6.02 | 74.81 | 6.65 | 18.54 |

TABLE 1-continued

| Sample | | Elemental Analysis | | | | XPS | | |
|---|---|---|---|---|---|---|---|---|
| | | C (%) | H (%) | N (%) | O (%) | C (%) | N (%) | O (%) |
| N-graphene | Calcd | 100.0 | 0.00 | 0.00 | 0.00 | 100.0 | 0.00 | 0.00 |
| | Found | 98.32 | BDL* | 0.12 | BDL* | 95.16 | 1.73 | 1.78 |

*BDL = Below detection limit.

As shown in Table 1, XPS measurement values show surface composition of carbon, oxygen and nitrogen and clearly represent the presence of nitrogen in N-graphene obtained by the heat treatment under nitrogen atmosphere at 900° C. for 2 hours. The elemental analysis represents the same result.

Figure 2:
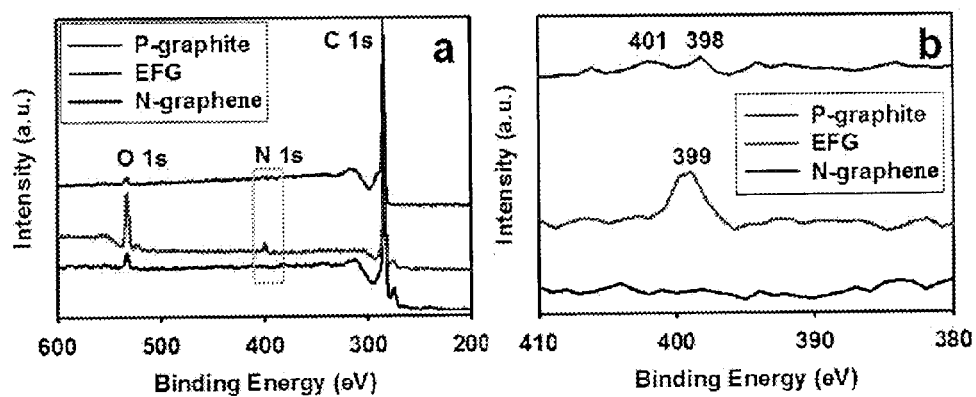
FIG. 2 shows XPS spectra for graphite (P-graphite), organic material-doped graphene (EFG) and N-graphene.

FIG. 2 is XPS spectra in which 2a is the whole spectra and 2b is a magnified spectra of a N 1s portion which is a part of the whole spectra. Particularly, upon reviewing N-graphene in FIG. 2b, they show peaks at 398 eV and 401 eV, which are peaks corresponding to pyridine-like nitrogen and pyrrolic-like nitrogen, respectively. From these peaks, it can be confirmed that nitrogen is doped on graphene.

Experimental Example 2

Field Emission Scanning Electron Microscopy

Figure 3:
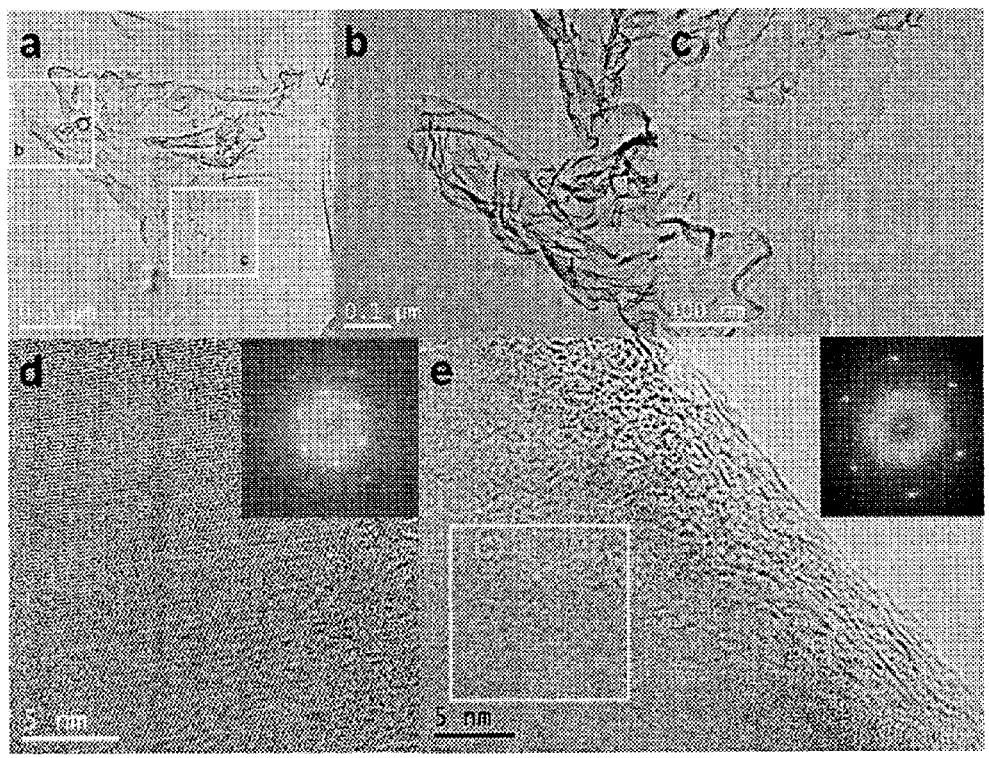
FIG. 3 is a field emission scanning electron microscope image obtained after a carbon-coated grid is dipped in a dispersion solution of organic material-grafted graphene.

A small amount of organic material-grafted graphene (EFG) obtained in the example 1-1 was dispersed in N-methyl-2-pyrrolidone (NMP) to obtain organic material-grafted graphene dispersion solution. Pure carbon-coated grid was dipped in the dispersion solution. Then, an image of the field emission scanning electron microscopy (FEI Tecnai G2 F30 S-Twin, operating voltage: 200 kV) obtained therefrom is shown in FIG. 3.

From FIGS. 3a to 3c, the presence of wrinkled graphene-like sheets can be confirmed. FIG. 3d is a high magnified image of a basal plane, from which a high crystalline graphene structure can be confirmed. This means that the basal plane is not functionalized by functionalization using the organic material and also not damaged. FIG. 3e is an image obtained by magnifying the edge of organic material-grafted graphene at high magnification, which shows single layer graphene sheets including a high crystalline interior plane and an organic material portion exclusively located at the edge. The electron diffraction patterns clearly represent that organic material-grafted graphene consists of individual graphene and graphene-like sheets.

Experimental Example 3

Raman Spectrum

Figure 4:
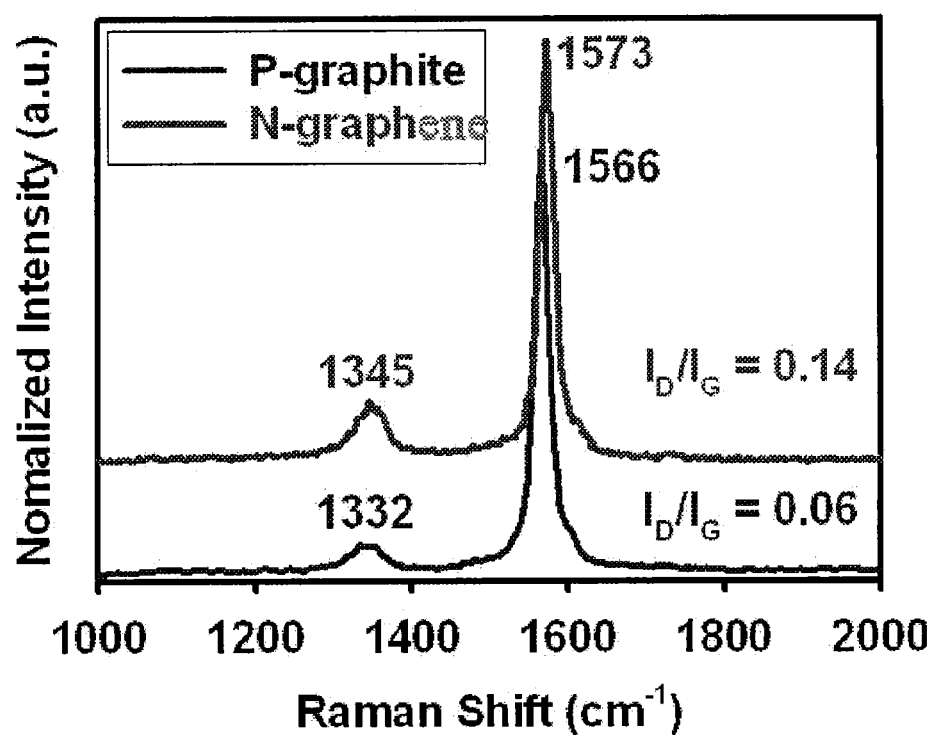
FIG. 4 shows Raman spectra of P-graphite and N-graphene, respectively.

Raman spectrum analysis for graphite used in the example 1-1 and N-graphene obtained in example 1-2 was conducted using Bruker Fourier-transform spectroform spectrophotometer IFS-66/FRA106S, 46 mW argon-ion laser (1064 nm) being used as an excitation source. The resultant spectra is shown in FIG. 4. The ratio of $I_D/I_G$ in graphite (P-graphite) and nitrogen-doped graphene (N-graphene) was identified to be 0.06 and 0.14, respectively. This means that defect ratio is slightly increased due to nitrogen doping in N-graphene.

Experimental Example 4

Atomic Force Microscopy

A small amount of organic material-grafted graphene (EFG) obtained in the example 1-1 was dispersed in THF to obtain organic material-grafted graphene dispersed solution. A drop of the solution was placed on a silicon wafer which was then dried in air. An atomic force microscope (Veeco Multimode V) image thereof and topographic height profiles corresponding thereto are shown in FIG. 5.

Figure 5:
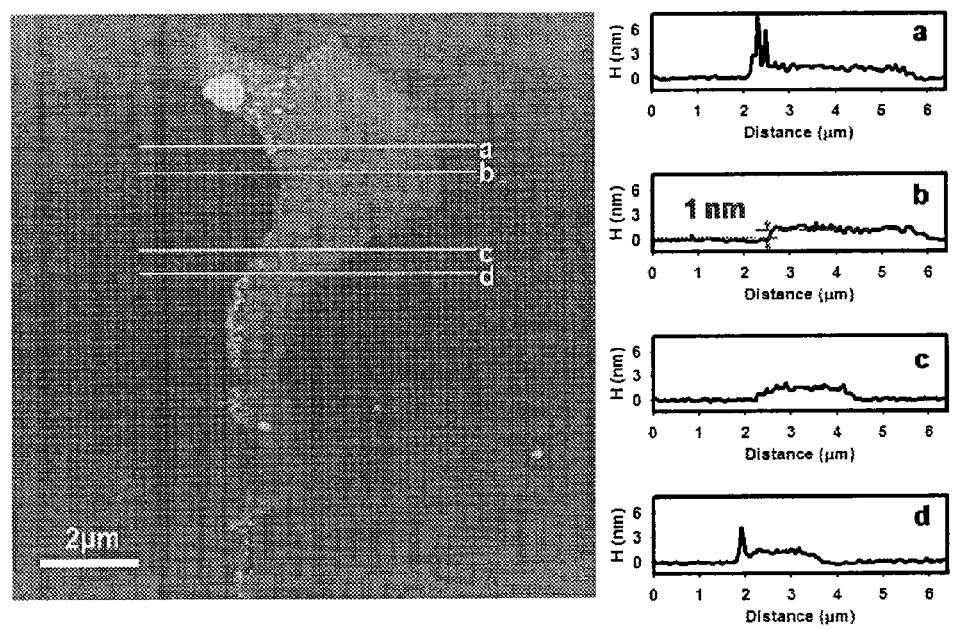
FIG. 5 shows an atomic force microscope image obtained after a dispersion solution of organic material-grafted graphene in tetrahydrofuran (THF) was drop-coated on a silicon wafer.

From FIG. 5, the presence of the graphene-like structure with the layer height of 1 or less nm could be verified. As expected, the height at the edge of the graphene sheet is higher than that of the inner layer because the functionalization took place mostly at the edge of the graphite.

Experimental Example 5

Themogravimetric Analysis

Figure 6:
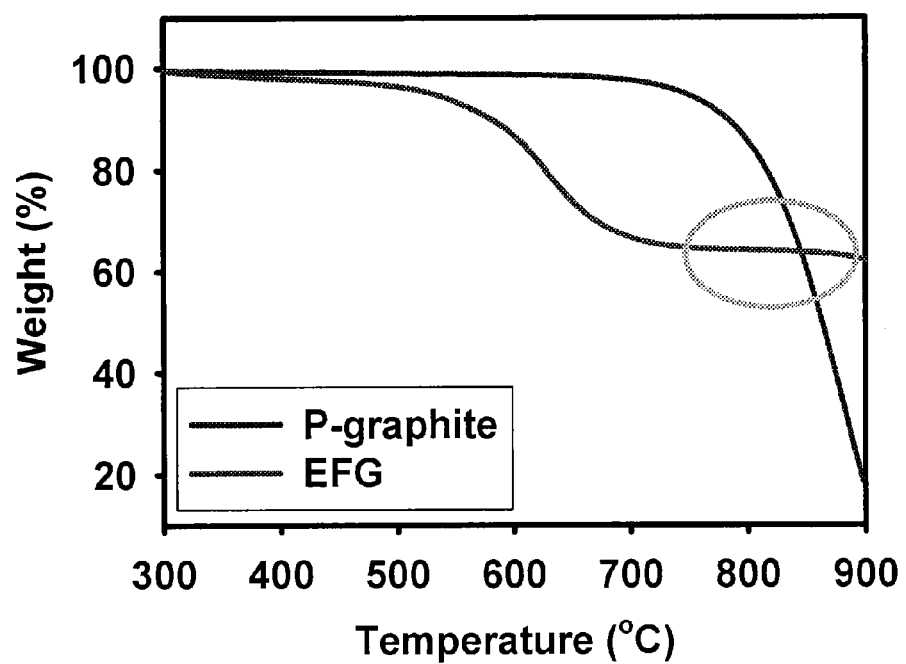
FIG. 6 is a graph showing results of thermogravimetric analysis of P-graphite and organic material-grafted graphene (EFG).

The results of thermogravimetric analysis (TA Hi-Res TGA 2950 Thermogravimeter, heating rate: 10° C./minute, in air) for the graphite (P-graphite) used in the example 1-1 and the organic material-grafted graphene (EFG) obtained in the example 1-1 are shown in FIG. 6.

According to FIG. 6, the functionalization degree can be presumed from the weight loss near 800° C. In addition, it can be verified that thermal stability of organic material-grafted graphene (EFG) is higher than that of graphite at a temperature of 850° C. or more. This means that the organic material portion on organic material-grafted graphene (EFG) thermally recover damage on the carbon frame during the heat-treatment.

In addition, according to the FIG. 6, it can be verified that during the heat-treatment, the organic material portion at the edge of organic material-grafted graphene (EFG) acts as feedstock for in-situ N-doping and C-welding and thus can convert organic material-grafted graphene (EFG) to N-graphene.

The N-graphene obtained as a result of the heat-treatment can be usefully used as an electrocatalytic catalyst for oxygen reduction reaction.

Experimental Example 6

Cyclic Voltammogram

Figure 7:
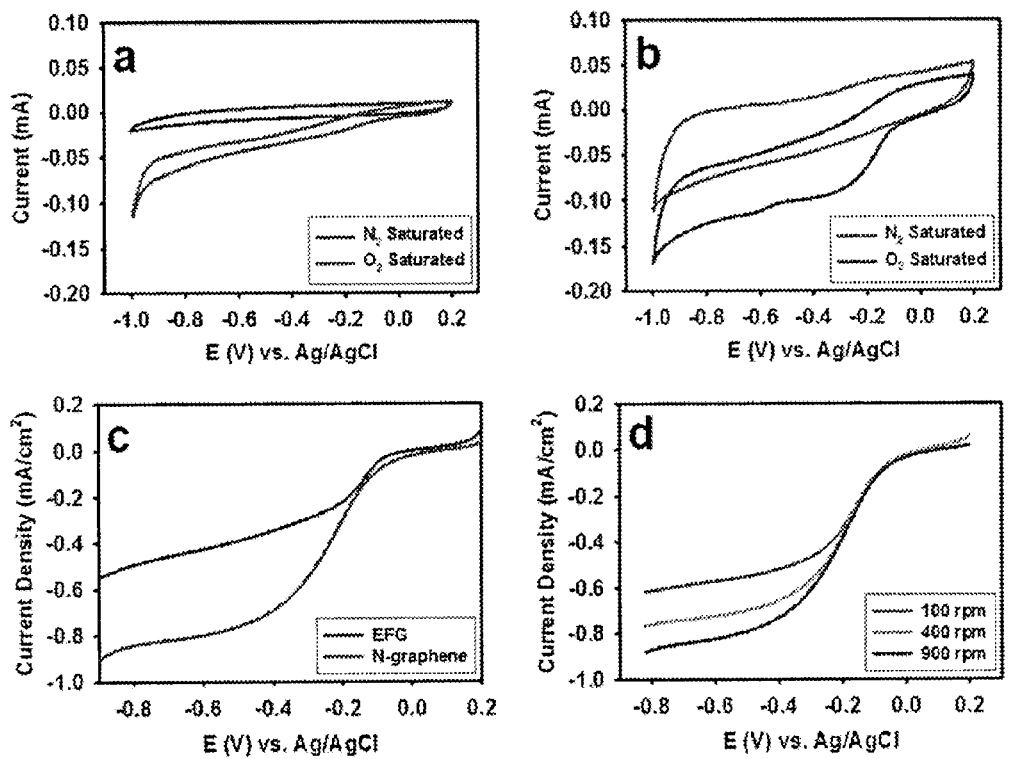
FIG. 7 is a graph showing a cyclic voltammogram of organic material-grafted graphene (EFG) film and N-graphene film formed on a glassy carbon (GC) electrode.

Cyclic voltammogram of as-cast EFG film casted on glassy carbon (GC) electrode in 0.1 M aqueous potassium hydroxide (KOH) solution saturated with $N_2$ or $O_2$ with a scan rate of 0.1 V/s. is shown in FIG. 7a. It can be verified that EPG in aqueous potassium hydroxide solution saturated with $N_2$ shows featureless voltammetric currents within a potential range of −1.0 to 0.2 V. In contrast, with reference to FIG. 7c described below, it can be verified that when the electrolyte solution is saturated with $O_2$, the reduction of $O_2$ occurs at the potential of −0.15 V.

Cyclic voltammogram of N-grasphene film on a glassy carbon (GC) electrode in 0.1 M aqueous potassium hydroxide (KOH) solution saturated with $N_2$ or $O_2$ with a scan rate of 0.1 V/s. is shown in FIG. 7b. The similar oxygen reduction activity as in FIG. 7a can be verified for N-graphene.

FIG. 7c shows rotating disk electrode voltammograms of the EPG film and N-graphene film formed on glassy carbon in 0.1 M aqueous potassium hydroxide solution saturated with $O_2$ at a rotation rate of 900 rpm and at a scan rate of 0.01 V/s. It can be verified that oxygen reduction activity of N-graphene is more pronounced than that of EFG.

FIG. 7d shows rotating disk electrode voltammogram of N-graphene film formed on glassy carbon in 0.1 M aqueous potassium hydroxide solution saturated with $O_2$ at different rotation rates of 100, 400 and 900 rpm and at a scan rate of 0.01 V/s. It can be verified that oxygen reduction activity of N-graphene is further superior at the higher rotation rate.

Experimental Example 7

Electrochemical Stability Measurements

The present inventors investigated the electrochemical stability under oxygen reduction reaction conditions of the N-graphene in $O_2$-saturated KOH for 1 day using sequential cyclic voltammetry.

Figure 8:
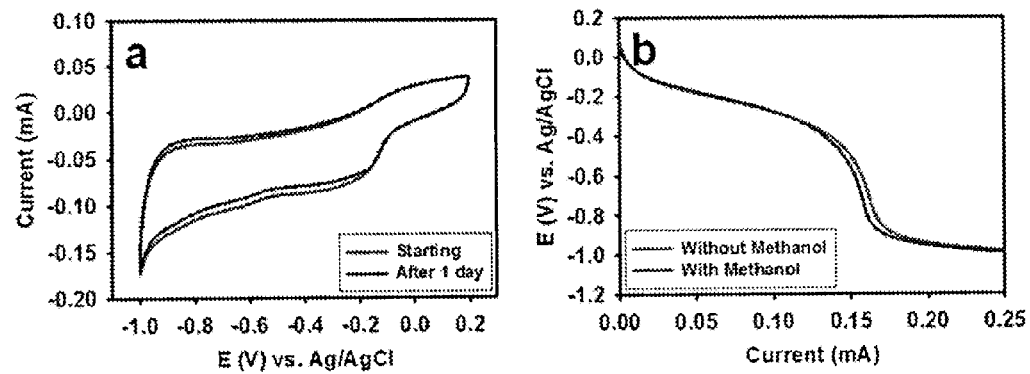
FIG. 8 is a graph showing a result of measuring electrochemical stability of N-graphene film formed on a glassy carbon electrode.

FIG. 8a shows that there was not any obvious change in the onset potential or in the kinetic current after continuous oxygen reduction reaction for 1 day, indicating that the catalytic sites of the graphene are rather stable in the base medium.

As can be seen from FIG. 8b, the open-circuit potential and steady-state output potential, along with the current output for N-graphene/GC electrode do not show any obvious change in an $O_2$ saturated 0.1M aqueous solution of KOH even after adding 2 wt % of methanol, which suggests that the corresponding effect of methanol crossover on the electrode is almost negligible.

The present invention includes a method of preparing organic material-grafted graphene comprising reacting an organic material having one or more amino groups and one or more functional groups selected from the group consisting of carboxylic acid group, amide group, sulfonic acid group, carbonylchloride group and carbonylbromide group with graphite in a reaction medium containing polyphosphoric acid/phosphorus pentoxide. This method may be the simplest, but most efficient one that is capable of large-scale exfoliation of three-dimensional graphite into two-dimensional graphene-like sheets without introducing any oxygen-containing functional groups on the basal plane of the graphene. In addition, the oxygen-free N-graphene/GC electrode can be prepared by heat treating the organic material-grafted graphene, and the resultant N-graphene/GC electrode can carry out very excellent oxygen reduction reaction.

Hereinbefore, the present invention was described in reference to illustrated examples, however, they are only illustrative. It is to be appreciated that those skilled in the art can change or modify the embodiments without departing from the scope and spirit of the present invention.

What is claimed is:

1. A method of preparing nitrogen doped-graphene comprising 1) reacting an organic material having one or more amino groups and one or more functional groups selected from the group consisting of carboxylic acid group, amide group, sulfonic acid group, carbonylchloride group and carbonylbromide group with graphite in a reaction medium containing polyphosphoric acid and phosphorus pentoxide-, thereby the graphite being exfoliated with the functional group of the organic material grafted to the graphite to prepare organic material-grafted graphene; and 2) heat treating the prepared organic material-grafted graphene at a temperature of 300 to 1,200° C.

2. The method of preparing nitrogen-doped graphene according to claim 1, wherein the organic material is alkane having 1 to 13 carbon atoms, alkene having 2 to 13 carbon atoms, alkyne having 2 to 13 cabon atoms, cycloalkane having 3 to 13 carbon atoms, arene having 7 to 19 carbon atoms or arylalkane having 7 to 19 carbon atoms, which have amino groups and the above functional groups, wherein the alkane, the alkene, the alkyne, the cycloalkane, the arene and the arylalkane are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, and phenoxy or the combination thereof.

3. The method of preparing nitrogen-doped graphene according to claim 1, wherein the organic material is aminobenzoic acid, diaminobenzoic acid, aminobenzoamide or diaminobenzoamide, which are unsubstituted or substituted with a substituent selected from the group consisting of halo, nitro, amino, cyano, mercapto, hydroxy, alkyl having 1 to 4 carbon atoms, alkoxy having 1 to 4 carbon atoms, formyl, alkylcarbonyl having 1 to 4 carbon atoms, phenyl, benzoyl, and phenoxy or the combination thereof.

4. The method of preparing nitrogen-doped graphene according to claim 1, wherein the organic material is a compound selected from the group consisting of 3-aminobenzoic acid, 4-aminobenzoic acid, 3-(4-aminophenyl)benzoic acid, 3-(3-aminophenyl)benzoic acid, 4-(4-aminophenyl)benzoic acid, 4-(3-aminophenyl)benzoic acid, 5-aminoisophthalic acid, 3-(4-aminophenoxy)benzoic acid, 3-(3-aminophenoxy)benzoic acid, 4-(4-aminophenoxy)benzoic acid, 4-(3-aminophenoxy)benzoic acid, 3,4-diaminobenzoic acid, 3,5-diaminobenzoic acid, 3-aminobenzoamide and 4-aminobenzoamide.

5. The method of preparing nitrogen-doped grapheme according to claim 1, wherein the heat-treatment is conducted for 10 minutes to 12 hours.

6. The method of preparing nitrogen-doped graphene according to claim 1, wherein the heat-treatment is conducted under the atmosphere of gas selected from the group consisting of methane, hydrogen, nitrogen, helium, neon and argon or the combination thereof.

* * * * *

UNITED STATES PATENT AND TRADEMARK OFFICE
CERTIFICATE OF CORRECTION

| | | |
|---|---|---|
| PATENT NO. | : 8,575,335 B2 | Page 1 of 1 |
| APPLICATION NO. | : 13/077777 | |
| DATED | : November 5, 2013 | |
| INVENTOR(S) | : In Yup Jeon et al. | |

It is certified that error appears in the above-identified patent and that said Letters Patent is hereby corrected as shown below:

On the Title Page, item (75)
THE CORRECT NAME IS "JONG BEOM BAEK."

Signed and Sealed this
Thirtieth Day of June, 2015

Michelle K. Lee
*Director of the United States Patent and Trademark Office*